(12) United States Patent
Fernandez Garcia et al.

(10) Patent No.: US 10,009,593 B2
(45) Date of Patent: Jun. 26, 2018

(54) DEVICE AND METHOD FOR OBTAINING DENSITOMETRIC IMAGES OF OBJECTS BY A COMBINATION OF RADIOLOGICAL SYSTEMS AND DEPTH-SENSING CAMERAS

(71) Applicants: CONSEJO SUPERIOR DE INVESTIGACIONES CIENTIFICAS (CSIC), Madrid (ES); UNIVERSIDAD POLITECNICA DE VALENCIA, Valencia (ES); UNIVERSIDAD DE VALENCIA, Valencia (ES)

(72) Inventors: Avelina Fernandez Garcia, Paterna (ES); German Vicente Rodrigo Garcia, Paterna (ES); Francisco Javier Albiol Colomer, Paterna (ES); Antonio Jose Albiol Colomer, Valencia (ES); Alberto Albiol Colomer, Valencia (ES)

(73) Assignees: CONSEJO SUPERIOR DE INVESTIGACIONES CIENTIFICAS (CSIC), Madrid (ES); UNIVERSIDAD POLITÉCNICA DE VALENCIA, Valencia (ES); UNIVERSIDAD DE VALENCIA, Valencia (ES)

( * ) Notice: Subject to any disclaimer, the term of this patent is extended or adjusted under 35 U.S.C. 154(b) by 266 days.

(21) Appl. No.: 14/418,608

(22) PCT Filed: Jul. 12, 2013

(86) PCT No.: PCT/ES2013/070502
§ 371 (c)(1),
(2) Date: Jan. 30, 2015

(87) PCT Pub. No.: WO2014/020202
PCT Pub. Date: Feb. 3, 2014

(65) Prior Publication Data
US 2015/0222875 A1  Aug. 6, 2015

(30) Foreign Application Priority Data

Jul. 31, 2012 (ES) .................................. 201231243

(51) Int. Cl.
*H04N 13/02* (2006.01)
*H04N 17/00* (2006.01)
(Continued)

(52) U.S. Cl.
CPC ....... *H04N 13/0203* (2013.01); *A61B 6/5247* (2013.01); *G06T 5/001* (2013.01);
(Continued)

(58) Field of Classification Search
CPC .............. H04N 13/0203; H04N 17/002; G06T 7/0051; G06T 17/00; G06T 5/001; G06T 15/08; G06T 7/55
(Continued)

(56) References Cited

U.S. PATENT DOCUMENTS 5,774,521 A * 6/1998 Close ..................... G01N 23/04
378/62
7,801,350 B2  9/2010 Le Bras et al.
(Continued)

FOREIGN PATENT DOCUMENTS

EP  1 684233  7/2006

OTHER PUBLICATIONS

International Search Report issued Nov. 19, 2013 in International (PCT) Application No. PCT/ES2013/070502.
(Continued)

*Primary Examiner* — Hee-Yong Kim
(74) *Attorney, Agent, or Firm* — Wenderoth, Lind & Ponack, L.L.P.

(57) ABSTRACT

A device and a method for obtaining densitometric images which comprise at least one radiological device, at least one
(Continued)

depth sensor, and image processing means, which combine the radiological absorption information from the set of recorded radiological images obtained with the radiological systems with the distances of the traversed material, provided by the three-dimensional reconstruction of the objects obtained by means of the depth sensors.

14 Claims, 7 Drawing Sheets (51) Int. Cl.
  *G06T 5/00*   (2006.01)
  *G06T 7/00*   (2017.01)
  *G06T 17/00*   (2006.01)
  *H05G 1/26*   (2006.01)
  *G01N 23/04*   (2006.01)
  *G06T 19/00*   (2011.01)
  *G06T 15/08*   (2011.01)
  *G06T 11/00*   (2006.01)
  *G06T 7/55*   (2017.01)
  *A61B 6/00*   (2006.01)

(52) U.S. Cl.
CPC .............. *G06T 7/55* (2017.01); *G06T 11/005* (2013.01); *G06T 15/08* (2013.01); *G06T 17/00* (2013.01); *G06T 19/00* (2013.01); *H04N 17/002* (2013.01); *A61B 6/466* (2013.01); *A61B 6/501* (2013.01); *A61B 6/5211* (2013.01); *G06T 2207/10028* (2013.01); *G06T 2207/10116* (2013.01); *G06T 2210/41* (2013.01); *G06T 2211/416* (2013.01)

(58) Field of Classification Search
USPC .......................................................... 348/46
See application file for complete search history.

(56) References Cited

U.S. PATENT DOCUMENTS

| 2006/0113482 | A1* | 6/2006 | Pelizzari | ............. | A61N 5/1049 |
| | | | | | 250/370.09 |
| 2010/0020080 | A1 | 1/2010 | Iwanaga | | |
| 2012/0026291 | A1 | 2/2012 | Lee | | |
| 2014/0016750 | A1* | 1/2014 | Kang | .................... | A61B 6/544 |
| | | | | | 378/62 |

OTHER PUBLICATIONS

Supplementary European Search Report dated Jun. 30, 2015 in corresponding European patent application No. 13 82 5508.8.
Ismail Mahmoud et al: "3D-guided CT reconstruction using time-of-flight camera" (Medical Imaging 2011: Visualization, image-guided procedures and modeling).

* cited by examiner

DEVICE AND METHOD FOR OBTAINING DENSITOMETRIC IMAGES OF OBJECTS BY A COMBINATION OF RADIOLOGICAL SYSTEMS AND DEPTH-SENSING CAMERAS

OBJECT OF THE INVENTION

The present invention, as expressed in the title of this descriptive document, firstly refers to a device for obtaining densitometric images of objects by combining radiological systems and depth cameras. Secondly, it refers to the method which, by means of the mentioned device, obtains densitometric images of objects using a combination of radiological systems and depth cameras. In addition, various uses of the method and procedure mentioned above are provided. The main fields of application of the device and method described herein are those of industry, medical and security, particularly the food quality control, quality control of industrial pieces and the improvement of radiological medical devices. Note that throughout the present document when talking about objects, individuals and scenes are also include, being able to apply the present invention indistinctly on any of them.

BACKGROUND OF THE INVENTION

The image formation model allows mathematically characterizing the process by which a point of the scene is projected onto an image.

Depending on the required accuracy and the application different types of formation models such as "pinhole" camera models, thin lens or thick lens are used.

The "pinhole" camera model (FIG. 3) is the simplest and the most used in the area of computer vision.

Among the main model parameters are the optical center or center of projection and the focal length which is the distance between the image plane and the optical center. The optical center is generally used as the origin of the coordinate system relative to a camera. In this model all points of FIG. 3 contained in any of the dotted lines are projected onto the same point on the image plane. Therefore, each point in the image represents a line in space that contains all the points projected on it. In stereo-vision this important property is used to be able to obtain the 3D coordinates of a point by triangulation (a straight line for each camera).

The "pinhole" camera model ("Multiple View Geometry in Computer Vision", Hartley, R. I. and Zisserman, A.) may be too simple when the lens used in the camera produces aberrations in the projected image. Some of the most common aberrations include: spherical aberration, astigmatism, radial/tangential distortion and field curvature.

The set of all the parameters which allow modelling the projective process and the distortions caused by the lenses are known as intrinsic parameters of the camera.

Figure 5:
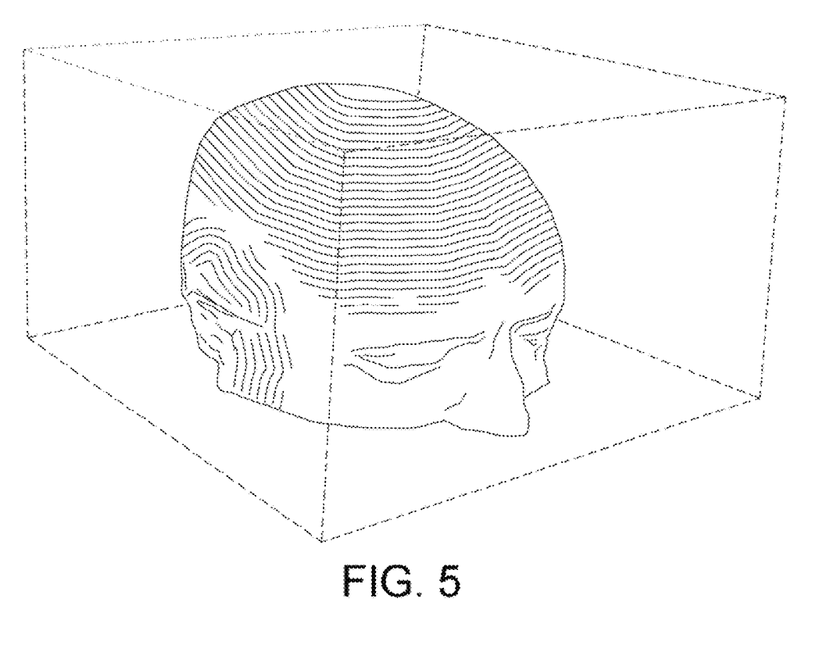
FIG. 5.—Shows a reconstruction of the surface of a human head by the use of depth cameras according to the state of the art.

Depending on the camera type the information projected in each point of the image may have different nature. For example, in an RGB image, each pixel provides information about the interaction zone of the incident light that is reflected to the plane of the camera (FIG. 5). In X-ray images, each pixel corresponds to the attenuated intensity due to absorption and diffraction phenomena between two surfaces limiting a volume.

The depth cameras are sensors that allow to create two-dimensional images in which each pixel contains the information of the distance between the point of the scene represented, and the plane of the camera. Sometimes, after a calibration process, it is possible to obtain the three spatial coordinates of the scene points with depth information.

There are multiple techniques for obtaining the depth of a scene. A first classification would distinguish between passive or active techniques. In the first case depth is obtained in most cases by using triangulation. For this, the images obtained by two or more RGB cameras are used and the correspondence problem is solved. The fundamental advantage of the passive methods is that special lighting conditions are not required and they are suitable for working outdoors in daylight. The disadvantage of passive cameras is that the correspondence problem is difficult to solve in both intensity and color homogenous zones.

In the case of active techniques the scene is illuminated artificially with a light pattern that by means of adequate processing, allows to determine the depth.

One of the pioneering techniques in this field illuminates the scene through a linear light beam. The deformation of the projection of the beam that impacts with objects in the scene can be related to the depth by triangulation if the position of the light source and the camera that captures the image are known. By the relative movement of the light beam with respect to the objects to be measured it is possible to obtain a set of profiles that form the depth image. The drawback of this technique is that the acquisition time of a depth image is large because in every instant solely one intensity profile is obtained.

An alternative way to obtain the depth image with a single image is to use structured light. In this case a known pattern of light such as a set of horizontal or vertical lines is usually projected. Again the analysis of pattern deformations allows to know the depth in many profiles.

Time of flight cameras employ an alternative technique similar to the one used in radar systems. In this case a specific sensor is used to measure the time of flight of a light pulse. The advantage over radar systems is that it is possible to obtain the depth of all the image points simultaneously and a sweeping of a spot beam is not necessary.

Recently a new type of low cost depth cameras appeared in the market. They use a different type of structured light known as coded light. Although these cameras were initially designed for leisure-related applications, its low cost has made possible that a great amount of new applications in many different areas appear (U.S. 2010/0199228 A1, Kinect patent). Such cameras are also known as RGB-D, this is because each point provides information about its color and depth. This is possible because the coded light pattern is in the near infrared.

3D cameras have numerous applications in fields such as industrial design, and medicine. In these cases either the cameras are used for registration or for object modelling. In other fields of application such as the video surveillance or assisted driving, the depth information is very useful to overcome ambiguities that are very difficult to solve using only the information of a conventional RGB image.

The set of systems for the reconstruction of the surface of an object is what is called "depth camera". If this measuring system includes the texture of the object it is called "texture and depth camera".

The X-rays (and gamma rays) techniques are commonly used in non-destructive analysis (Industrial Radiology: Theory and Practice R. Halmshaw; Niet-destructief onderzoek ISBN 90-407-1147-X (Dutch). WJP Vink, Non-destructive analysis. Application of machine vision to food and agriculture: a review Davies ER) since the early twentieth century, both in clinical diagnosis and inspection of objects and have led to major technological advances in the development of detectors and production methods. The radiographic images are obtained by placing a natural or artificial source of gamma or X rays passing through a part or all the examined object, and a generally flat or linear detector at the other side. Absorption differences due to the nature of the material and material thickness generate an image of intensities on the detector.

The fundamental difference between X-rays and gamma-rays is that the first are derived from a source which generates a continuous spectrum of photons, while gamma rays from natural de-excitation of atomic nucleus or deep layers of electrons in the atom have known energies, namely monochromatic sources.

The use of radiographic X-ray sources has the advantage that intensity can be modulated and the emission can automatically be cut, while gamma sources cannot cut their emissions because this is a natural process that follows a varying intensity over time:

$$I = I_0(t_0)e^{-wt}$$

where "w" is the inverse of the half-life of the isotope, "$I_0(t_0)$" is the source intensity measured at time "$t_0$" and "t" is the time where the current measurement is performed.

This feature allows applications such as measuring the diffusion of tracers in live systems and allows applications such as the SPECT (cameras that detect the projection of the isotope in a plane) or PET (geometrically paired cameras that detect coincidences of photons from positrons produced by the decay of the nucleus).

There are two ways commonly used to obtain the intensity of the source that passes through the scene, or the total intensity is measured without discriminating the individual energy of every photon or the individual energy of every photon is counted and measured by using gamma cameras. This latter type of techniques is applied in the aforementioned PET and SPECT applications. When X-rays interact with matter they are partly absorbed and partly transmitted. The probability of interacting with the material depends on the electron density which is a function that depends on the incident photon energy, and on the elemental composition (Z or atomic number) of the material.

Thus the absorption of X-rays depends on the distance they cross, and the characteristics of the material. The transmitted intensity is determined by the following expression:

$$I = I_0 \int e^{-k(r)x} dx$$

where "$I_0$" is the incident intensity, "k(r)" is a constant that depends on the electron density of the material and "x" is the distance crossed. Because the sources are usually punctual, the radiation intensity "I" must be multiplied by a geometric factor that depends on the square of the inverse of the distance "r" to the source. The absorption coefficient is additive, then in a material composed by different elements:

$$k = \Sigma \omega_i k_i$$

where "$\omega$" refers to the fraction of each component and the subscript "i" indicates the "k" characteristic for each of them. To find the distance "x" in the acquisition of planar X-ray images is not possible ("The X-ray Inspection" Dr. Ing. M. Purschke. Castell-Verlag GmbH) unless the geometry is known.

From the point of view of the end user, it is necessary to establish an optimization protocol of both, the maximum energy of the beam and its intensity, in order to prevent the saturation of the image by an excess of intensity or the lack of contrast by default therein. Optimal working parameters depend on the density or density variations expected.

In clinical diagnostic environments, for example, the calibrations are performed by means of mannequins with known densities. Once the equipment is calibrated, the defined parameters are used to highlight different injuries and to analyze the state of bones and tissues, or to locate foreign bodies.

In some cases to calibrate the detector response, easily detectable elements with different thicknesses are included in the scene either manually or automatically to establish a link between the measured intensity in the pixel of the detector and the material thickness.

Another technique is the use of X-ray sources that emit at two different energies (multi-voltage). These techniques rely on the fact that X-ray absorption in the medium is different and depend on the electron density of the material and the energy of the X-ray beam. Comparing the images of the same scene acquired at different voltages one can get information on the material composition, being the method able to perform a densitometric study. This method that allows the evaluation by comparing (FIG. 1) the distance travelled by the radiation in the material is inaccurate because the measures obtained are relative. It also requires extra steps and to have either time for the two measurements or to have two radiological devices.

In general, the image of X-rays or gamma rays obtained in a detector is a mixture of different frequencies (colors) from the emitting source. It is a multispectral image where multiple wavelengths overlap. For applications where it is necessary to select a small continuous band of wavelengths, diffraction techniques or radioactive sources of known energy are applied. The former have the disadvantage of drastically reducing the light intensity of the beam and the second has the disadvantages associated with the natural sources of gamma rays.

The resulting image has a camera equation characterized by the intrinsic parameters, i.e. distance from source to detector, radial corrections in case of use of image intensifiers, and some extrinsic parameters which locate the radiological system to a coordinate system.

Figure 2:
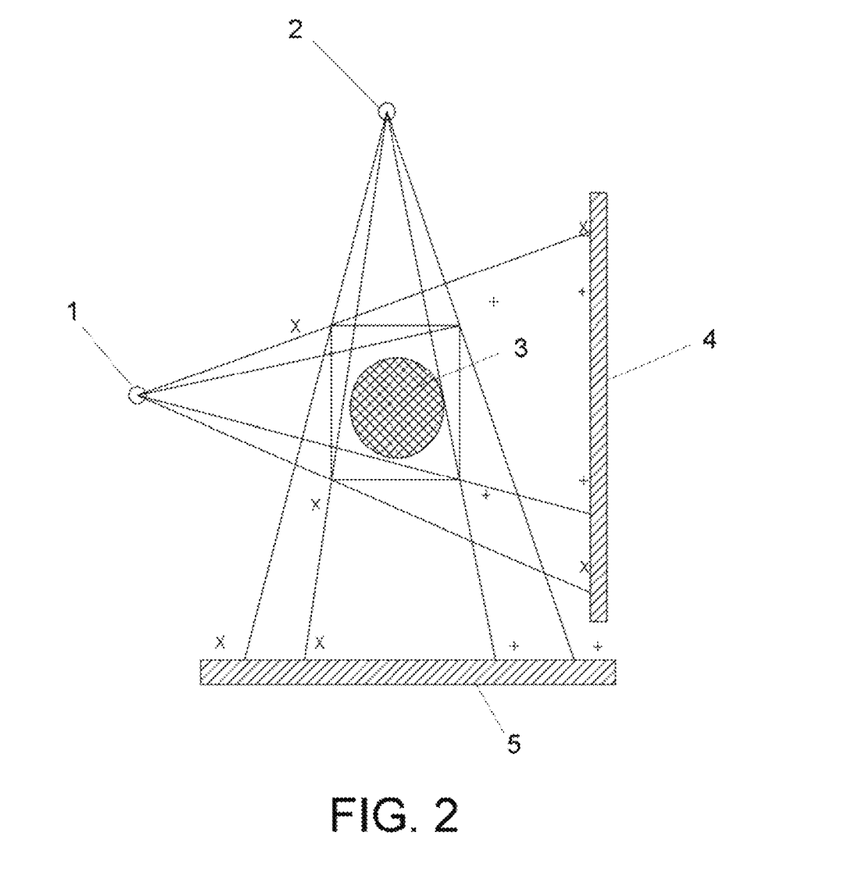
FIG. 2.—Shows the process, which belongs to the state of the art, for the registration of X-ray images using recognizable cross-shaped fiducials (x, +), for the camera equation of each projection.

When two radiographic images registered from different locations are combined, triangulation methods suitable to the visible light can be applied. This manual or automatic identification of scene elements in the two projections allows the reconstruction of the spatial position of the element ("Trajectory triangulation: 3D reconstruction of moving points from a monocular image sequence" Avidan and Shashua). Thus, the pixels obtained in the image cuts generate, by means of the implementation of algebraic methods, a stereoscopic image with three-dimensional information (FIG. 2).

The 3D image reconstruction can be performed from 2D images using image acquisitions from different angular positions ("tomography systems"). In these devices, the pixel size in the micrometer range is termed "micro-tomography systems." The image acquisition can be based on "gantry systems" with a detector or detectors and a source or sources of X-rays that rotates on its axis or in systems in which the scene rotates on its axis.

Sensors which provide planar images are detectors sensitive to the radiation intensity detected either in a plane or linearly arranged, but relying on the relative movement of the object and the detector, and synchronizing the displacement speed with the speed of reading. Although the calibration treatment of these images is slightly different to obtain the register, as in the first case you have a different focal for each vertical-horizontal orientation of the image, the mathematical differences in their treatment are not relevant.

The assembly between the image sensor and the source of X-rays or gamma rays is called 'radiological system', and provides 'radiological images'. If these images contain information related to a 'reference frame' they are called 'registered radiological images'.

As already mentioned, there are well-known techniques for image registration in the state of the art. The depth camera systems require knowing the calibration parameters of the camera to reconstruct the image. There are techniques that use identifiable and recognizable symbols by means of image processing which allow obtaining this matrix. These methods allow allocating a line in space for each pixel, on the basis of the distance between the focus and the center of the camera, as well as the rotation and translation matrix and the distortion coefficients. These systems are called "reference frame for depth cameras" in this document.

Figure 4:
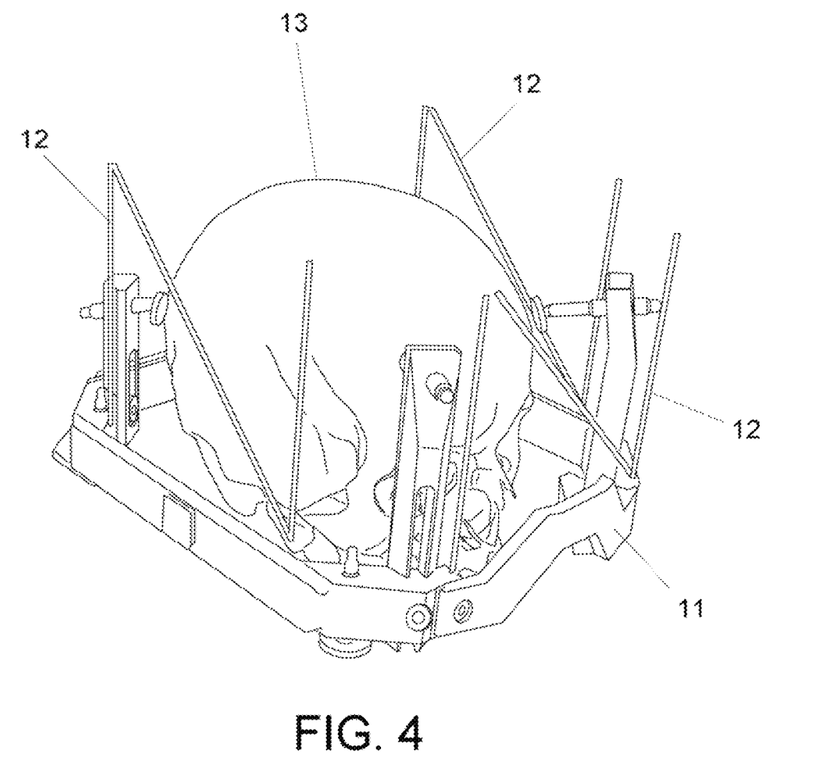
FIG. 4.—Shows a perspective image about a volumetric reconstruction of a human skull, showing a fiducial system for 3D volumes.

For the same purpose, in X-ray the calibration is performed using fiducial or marks systems that identify coordinates which are known and visible on different imaging modalities and are adapted to the various setting modes. In the case that the acquisition is made by volume, a technique used in medicine is the use of frames calibrated and adapted to the patient (FIG. 4). These systems are called "reference frame for radiological image" herein named as "reference frame".

The surface information obtained with different wavelengths in the visible region of the spectrum may be also used for texture analysis, i.e. to study periodic spatial distribution patterns that form the surface topography of the object locally.

Throughout herein, when two systems or devices images provide spatial information in the same coordinate system will be referred to as "registered systems or devices" and the images captured by such systems will be referred to as "registered images".

However in the state of the art devices integrating radiological systems and depth cameras working together to provide densitometric images of objects, scenes or individuals, are not found.

DESCRIPTION OF THE INVENTION

To achieve the objectives and avoid the drawbacks stated above, the invention consists of a device and a method for obtaining densitometric images of objects combining radiological systems and depth cameras.

A first object of the present invention is a device that obtains information from the surface of an object by using depth cameras or depth cameras with texture combined with one or more radiological systems. By registering the radiological system and depth cameras, spatial information in the analysis of X-ray images is introduced.

As additional information obtained in the process, the parameterization of the object surface is obtained. In applications where this surface is of interest, it may be further provided.

More specifically, the first object of the present invention is a device for obtaining densitometric images of objects by the combination of radiological systems and depth cameras. That device comprises at least:
  at least one radiological device, which provides a set of registered radiological images where the radiological images comprise information about the radiological absorbance of the objects;
  at least one depth sensor, which provides a set of registered depth images that allow the three-dimensional reconstruction of part of the surfaces that constitute the objects;
  image processing means that combine the information of radiological absorption of the set of radiological images with the width of the material traversed provided by the three-dimensional reconstruction of the objects.

In a particular embodiment of the invention, at least one of the depth sensors comprises tools for moving its relative position with respect to the rest of the device, while keeping the registration.

In another particular embodiment of the invention, at least one of the radiological systems comprises tools for moving its relative position with respect to the rest of the device, while keeping the registration.

In another particular embodiment of the invention, the device comprises a system of marks in pre-set fixed locations recognizable for the at least one radiological device and for the at least one depth sensor. This system of marks allows the calibration of the elements in the device to obtain densitometric images.

In another particular embodiment of the invention, the objects comprise frames of known materials, positioned in the proximity to said objects, that allow to filter the X-ray spectrum and to obtain regions of pixels with modulated energy in the same radiological image.

In another particular embodiment of the invention, at least one radiological system comprises a radiation source of gamma rays.

In another particular embodiment of the invention, the device for obtaining radiological images comprises a system of registered images that enables to incorporate texture information to the object surfaces.

In another particular embodiment of the invention, the radiation source comprises a radiotherapy accelerator.

In another particular embodiment of the invention, the device comprises at least one registered image in the visible light region of the spectrum for applying information on the texture to the object surface.

A second object of the invention is the method for obtaining densitometric images of at least one object by combination of radiographic images and depth cameras. Such a procedure is carried out by using the device described above.

This method includes the following steps:
  acquire at least one radiological image registered by at least one radiological system/device;
  generate the three-dimensional reconstruction of the object from the set of registered depth images acquired through the system to acquire depth images;
  calculate, for each pixel in the radiological image, a straight line in the space which represents that pixel;
  calculate one entry point and one exit point, corresponding to the intersection of each straight line calculated for each pixel in the radiological image with the surface obtained by the three-dimensional reconstruction of the object;
  calculate the width by the length of the segment joining the entry and exit points in the radiological image;
  combine, for each pixel in the radiological image, information on the length of the segment calculated with the information on the surface obtained from the three-dimensional reconstruction of the object.

In a particular embodiment of the invention, at least one sensor changes its relative position with respect to other components of the system, keeping the registration.

In another particular embodiment of the invention, at least one of the radiological systems changes its relative position with respect to other components of the system, keeping the registration.

In another particular realization of the invention, the method comprises a combination of the visible images of the objects with the three-dimensional image of the depth sensors, obtaining images with texture.

Furthermore, a third object of the present invention is the uses of the device and the process described above. Among the possible uses of the present invention and not limited only to them, its use is provided in the following systems or devices: axial tomography systems, micro-tomography systems, fluorescence spectrometry systems, systems of microspectrometry X-ray fluorescence, vibrational spectroscopy systems, systems of near-infrared spectroscopy, multispectral cameras systems, hyperspectral cameras systems, accelerators for radiotherapy, display systems, quality control systems, food, products and mechanical constructions inspection systems, side scatter correction systems (side scatter), inspection of mechanical pieces and support systems for diagnostic devices.

DESCRIPTION OF SEVERAL EXAMPLES OF REALIZATION OF THE INVENTION

Subsequently, a description of various embodiments of the invention is carried out, with an illustrative and non-limiting character, with reference to the notation adopted in the figures.

X-ray images do not provide information about the surface delimiting the inspected object. This information is relevant for the analysis of the density of the materials. Under certain circumstances, the geometry is known or can be obtained in a comparative way. But usually this information is not available, reducing the applicability of the X-ray images.

Figure 1:
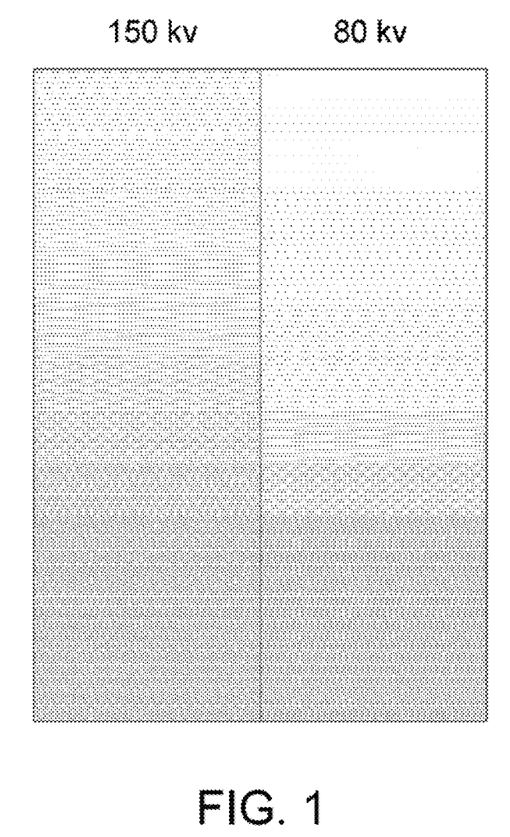
FIG. 1.—Shows contrasts obtained with calibrated patterns and different voltages in an X-ray tube.

The most common solution to this problem is the dual-energy X-ray absorptiometry, which involves the comparison of two X-ray images taken with different voltages. The cost of these devices, however, is high, because two X-ray sources and two detectors are required. Likewise this method does not allow to obtain spatial information of the scene. Another technique is the use of X-ray sources emitting at least two different energies (multi-voltage). The FIG. 1 shows the contrasts obtained with calibrated templates for two different voltages. Specifically, the comparison of the distances travelled by the radiation in the material for two different voltages, 150 kV and 80 kV, is presented, showing the material with higher electronic density in darker colors.

FIG. 2 shows the process for obtaining the registered X-ray images for the camera equation of each projection. This type of image registration is commonly used in clinical protocols. Thus, two X-ray sources (1, 2) are used to irradiate an object (3) provided with a recognizable cross-shaped fiducial system (x, +) which at the same time are projected on the radiation receptors (4, 5) respectively. To avoid the confusion in the spatial orientation of this application an extra fiducial could be set in any of the two types of fiducials.

Figure 3:
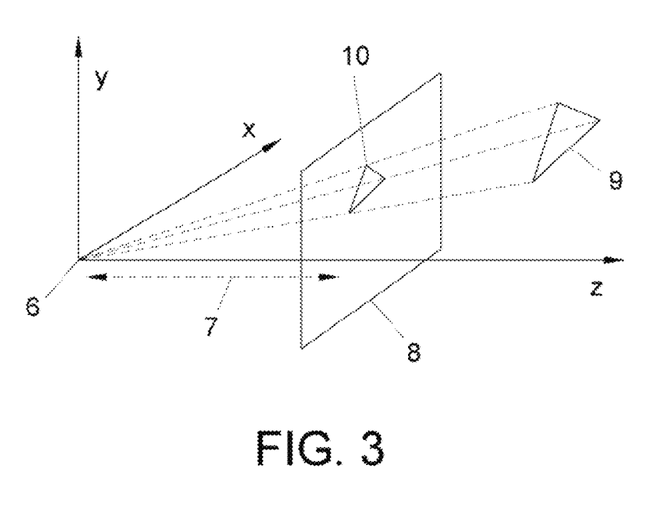
FIG. 3.—Shows the formation of images in the geometric pinhole camera model.

The projection process for the "pinhole" camera model is represented in FIG. 3. The optical center or projection center (6) and the focal length (7) which is the distance between the image plane (8) and the optical center (1) are among the main parameters of the model. The optical center (1) is generally used as the origin of the coordinate system referred to a camera. It shows how all the dots contained in any of the dotted lines are projected onto the same point (10) in the image plane (8). Therefore, each dot in the image (10) of the object (9) represents a straight line in the space that contains all dots which are projected (9) on said object (9).

A volumetric reconstruction of a human skull showing a fiducial system for 3D volumes is shown in FIG. 4. That fiducial system is fixed with a calibrated frame (11) that is adapted to the subject (13). "N-shaped" items (12) establish a recognizable pattern in computed tomography or magnetic resonance images. These fiducials facilitate the mathematical inference of the object surface, the human head in this case, for which the 3D coordinates must be expressed in the same reference system. For this, the inference is carried out by the combined use of patterns visible in both systems, the depth cameras, by locating elements of the scene, and the radiological systems.

The fiducial system and the calibrated frame are particular embodiments, being able to use other existing fiducial systems and frames available in the state of the art.

FIG. 5 shows a partial reconstruction of the surface of a human head obtained by depth cameras. The techniques used in this type of reconstruction are well-known in the state of the art.

Figure 6:
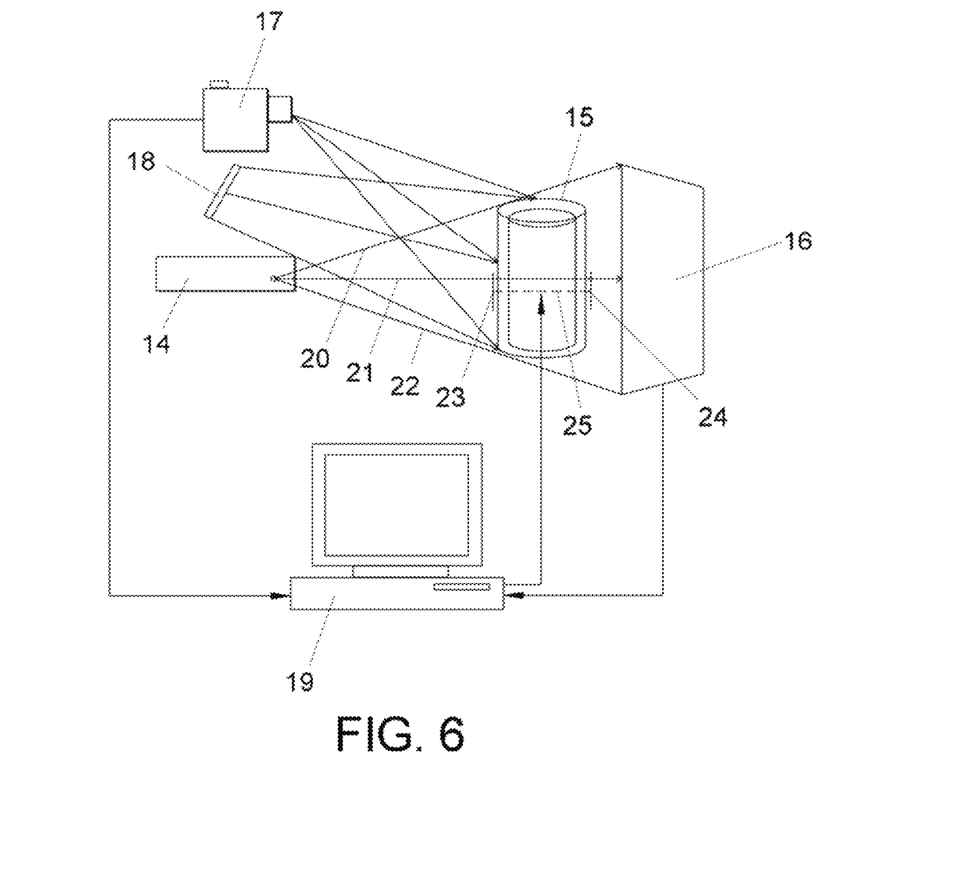
FIG. 6.—Shows a particular embodiment of the device object of the present invention.

FIG. 6 shows a particular embodiment of the device which is the object of the present invention. Specifically it includes a radiation source (14) that emits an X-ray or gamma ray beam on an object (15) from which a densitometric radiological image in a radiological receptor (16) want to be obtained. It also includes a depth camera (17) and a receptor (18) of the depth camera (17). That receptor (18) is responsible for providing the 3D reconstruction of the object (15). The device also includes a unit for image registration (19). Three beams (20, 21, 22) of X-rays or gamma rays irradiating the object, as an example, are represented. For the central beam (21) the width of the material passed through by the beam is represented, presenting an entry point into the object (23) and an exit point (24), defining the two points a straight line (25) which corresponds to the width of the material. Starting with the surface measured with the depth camera (17) and the receptor (18) and with the X-ray image captured by the source (14) and the receptor (16), for each pixel of the radiological image the equation of the line which represents each one of the pixels, is calculated. Taking that line (25) to the 3D reconstruction captured by the camera (17) and the receptor (18) the straight line is obtained (25) which defines the width of material traversed by the beam (21). Finally the information from the widths calculated for each pixel in the radiological image is used to correct the original radiological image.

Figure 7A:
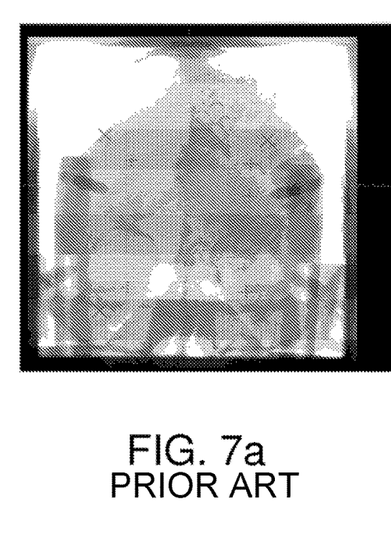
FIG. 7a.—Shows an X-ray image taken by conventional devices and techniques.
Figure 7B:
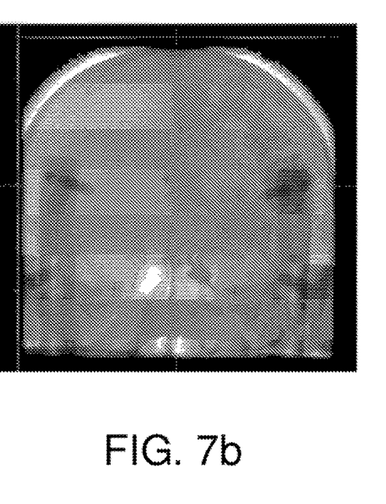
FIG. 7b.—Shows an X-ray image taken by the device and method object of the present invention.

The result of the preceding statements is clearly shown in FIGS. 7a and 7b where the same X-ray image taken by conventional devices and techniques (FIG. 7a) and by the device and method object of the present invention (FIG. 7b) are shown. So, based on the radiological image shown in FIG. 7a, and combining this image with the information provided by the surface reconstruction obtained with the depth cameras shown in FIG. 5, FIG. 7b is obtained, which proves that the dynamic range of the image has been compacted by representing density instead of absorption. Adjusting the dynamic range for visualization allows a simplification of the diagnostic systems.

The invention claimed is:

1. A device for obtaining densitometric images of objects by a combination of radiological systems and depth-sensing cameras, wherein the device comprises:
    at least one radiological device, which provides a set of registered radiological images, wherein the set of registered radiological images comprise radiological absorption information of the objects;
    at least one depth sensor that provides a set of registered depth images that allow three-dimensional reconstruction of surfaces that constitute the objects; and
    image processing means configured to calculate a distance of traversed material for each pixel of the set of registered radiological images, wherein the distance corresponds to an intersection of a straight line in space representing each pixel with a surface of a corresponding object of the objects, and to obtain a densitometric image of the corresponding object by calculating an electronic absorption in-depth density for each pixel, based on both the radiological absorption information of each pixel of the set of registered radiological images and corresponding calculated distances of traversed material.

2. The device for obtaining densitometric images, according to claim 1, wherein the at least one depth sensor comprises tools for moving a relative position of the at least one depth sensor with respect to a remainder of the device, while maintaining registration.

3. The device for obtaining densitometric images, according to claim 1, wherein at least one of the radiological systems comprises tools for moving from a relative position of the at least one of the radiological systems with respect to a remainder of the device, while maintaining registration.

4. The device for obtaining densitometric images according to claim 1, wherein the device further comprises a system of marks in pre-set fixed locations recognizable from the at least one radiological device and the at least one depth sensor, which allows calibration of the device for obtaining densitometric images.

5. The device for obtaining densitometric images according to claim 1, wherein the objects comprise, positioned in proximity, frames of known materials, that allow for filtering part of an X-ray spectrum and for obtaining regions of pixels with modulated energy in a same radiological image.

6. The device for obtaining densitometric images according to claim 1, wherein at least one of the radiological systems comprises a radiation source of gamma rays.

7. The device for obtaining densitometric images according to claim 1, wherein the device further comprises a system of registered images that enables incorporation of texture information to the surface of the corresponding object.

8. The device for obtaining densitometric images according to claim 1, wherein the device further comprises a radiation source comprising a radiotherapy accelerator.

9. The device for obtaining densitometric images according to claim 1, wherein the at least one depth sensor is configured for providing at least one registered image in a visible region of the corresponding object for applying information on a texture to the surface of the corresponding object.

10. The device for obtaining densitometric images according to claim 1, wherein the device is used in systems selected between:
    axial tomography systems;
    micro-tomography systems;
    fluorescence spectrometry systems;
    X-ray microfluorescence spectrometry;
    systems of vibrational spectrometry;
    systems of near-infrared spectroscopy;
    hyperspectral camera systems;
    radiotherapy accelerators;
    visualization systems;
    quality control systems;
    food, products and mechanical constructions inspection systems;
    side scatter correction systems;
    inspection systems for mechanical pieces; and
    support systems for diagnostics.

11. A method for obtaining densitometric images of at least one object by combination of radiological images and depth cameras, the method comprising:
    acquiring at least one registered radiological image by at least one radiological device;
    generating a three-dimensional reconstruction of the at least one object from a set of registered depth images acquired by at least one depth sensor;
    calculating, for each pixel of the at least one radiological image, a straight line in the space that represents the pixel;
    calculating one entry point and one exit point, corresponding to an intersection of each straight line calculated for each pixel of the at least one radiological image with a surface, obtained by the three-dimensional reconstruction, of the at least one object;
    calculating a length of a segment that joins the one entry point and the one exit point in the three-dimensional reconstruction;
    obtaining a densitometric image of the at least one object by calculating an electronic absorption in-depth density for each pixel, based on both a radiological absorption value of each one of the pixels of the at least one registered radiological image, and a corresponding calculated length of the segment that joins the one entry point and the one exit point in the three-dimensional reconstruction of the at least one object.

12. The method for obtaining densitometric images according to claim 11, wherein the at least one depth sensor changes its relative position with respect to a remainder of components of the device, thereby maintaining registration.

13. The method for obtaining densitometric images according to claim 11, wherein the at least one registered radiological device changes its relative position with respect to a remainder of the device, thereby maintaining registration.

14. The method for obtaining densitometric images according to claim 11, wherein the method further comprises combining visible images of the at least one object provided by the at least one depth sensor with the set of registered depth images, and obtaining registered depth images with texture.

\* \* \* \* \*